(12) United States Patent
Fischer (10) Patent No.: US 7,278,852 B2
(45) Date of Patent: *Oct. 9, 2007

(54) KIT OF SUB-KITS FOR PLACING A DENTAL POST

(75) Inventor: Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 12 days.

This patent is subject to a terminal disclaimer.

(21) Appl. No.: 11/097,631

(22) Filed: Apr. 1, 2005

(65) Prior Publication Data

US 2006/0223035 A1    Oct. 5, 2006

(51) Int. Cl.
*A61B 19/02* (2006.01)

(52) U.S. Cl. .................. 433/224; 433/102; 206/63.5

(58) Field of Classification Search .................. 433/49, 433/50, 81, 102, 224; 206/63.5, 369
See application file for complete search history.

(56) References Cited

U.S. PATENT DOCUMENTS

| | | | | |
|---|---|---|---|---|
| 3,358,826 A | | 12/1967 | Siegel | 206/63.5 |
| 3,660,901 A | | 5/1972 | Inoue | 32/40 |
| 4,293,074 A | | 10/1981 | Dunsky | 206/572 |
| 4,327,060 A | * | 4/1982 | Nisii | 422/300 |
| 4,353,694 A | | 10/1982 | Pelerin | 433/77 |
| 4,850,866 A | | 7/1989 | Gutierrez et al. | 433/72 |
| 5,127,832 A | | 7/1992 | Zdarsky | 433/102 |
| 5,150,788 A | * | 9/1992 | Weissman | 206/369 |
| 5,172,810 A | | 12/1992 | Brewer | 206/369 |
| 5,289,919 A | | 3/1994 | Fischer | 206/571 |
| 5,358,112 A | * | 10/1994 | Gardner | 206/369 |
| 5,453,010 A | * | 9/1995 | Klein | 433/221 |
| 5,516,287 A | | 5/1996 | Zdarsky | 433/102 |
| 5,692,609 A | | 12/1997 | Lin | 206/368 |
| 5,829,590 A | | 11/1998 | Klein | 206/369 |
| 5,921,775 A | * | 7/1999 | Buchanan | 433/102 |
| 5,964,592 A | | 10/1999 | Hites et al. | 433/221 |
| 5,967,778 A | * | 10/1999 | Riitano | 433/77 |
| 6,024,565 A | | 2/2000 | Sicurelli et al. | 433/102 |

(Continued)

OTHER PUBLICATIONS

EDS Product Packaging "Flexi-Post" system, no date available URL: http://www.edsdental.com/productpdfs/fpostprofile.pdf.

(Continued)

*Primary Examiner*—Ralph A. Lewis
(74) *Attorney, Agent, or Firm*—Workman Nydegger (57) ABSTRACT

A kit of dental sub-kits for use in placing a dental post in a prepared recess (e.g., a root canal) of a person's tooth. The kit includes a tray having an interior recess configured to removably receive therein a plurality of individual dental sub-kits. Each sub-kit may have an associated color, number, letter, or other marking to distinguish it from at least one other sub-kit within the kit. The color or marking associated with each sub-kit identifies the size of components contained within the sub-kit. Each sub-kit includes a finishing drill and one or more permanent dental posts. Each sub-kit may optionally include a starter drill and/or a dental post analog. Each sub-kit and its contents may be disposable or autoclavable.

20 Claims, 9 Drawing Sheets

U.S. PATENT DOCUMENTS

| | | |
|---|---|---|
| 6,312,258 B1 | 11/2001 | Ashman ..................... 433/172 |
| 6,331,112 B1 | 12/2001 | Lee ............................ 433/102 |
| 6,464,497 B2 | 10/2002 | Landoz ........................ 433/77 |
| 6,681,925 B2 * | 1/2004 | Fischer et al. ............. 206/63.5 |
| 6,827,576 B2 | 12/2004 | Karmaker et al. .......... 433/220 |
| 2003/0121811 A1 | 7/2003 | Roshdy ...................... 206/363 |
| 2004/0081940 A1 | 4/2004 | Roetzer et al. ............. 433/165 |
| 2004/0200748 A1 | 10/2004 | Klassen et al. ............. 206/368 |

OTHER PUBLICATIONS

Nordin Dental, "Zirix Zirconium dioxide ceramic post system"© 2004-2005 URL: http://www.nordin-dental.com.

Pearson Dental Supplies Catalog, Exatec Carbon Post System (Hahnenkratt), URL: http://www.pearsondental.com/catalog, Mar. 17, 2005.

E. Hahnenkratt GmbH, Post Restoration with System, © 2004 URL: http://ww.hahnenkratt.com.

MTI Precision Products, LLC, ME-4422 GyroTip Booklet, Apr. 5, 2004.

* cited by examiner

KIT OF SUB-KITS FOR PLACING A DENTAL POST

BACKGROUND OF THE INVENTION

1. The Field of the Invention

The present invention is in the field of endodontics. More particularly, the invention relates to the placement of dental posts used during placement of a crown or other dental prosthesis onto a patient's tooth.

2. The Relevant Technology

When performing a root canal, the dental practitioner will remove the pulp material forming the nerve of the tooth at issue, carefully prepare the canal that contained the nerve material and other pulp tissues, obturate or fill and seal the canal, and later insert a dental post into the root. The dental post serves to provide support for the coronal aspect of the tooth.

In determining which dental post to install, the dental practitioner considers the length, taper, and size required. In addition, the size of the drills used in preparing a post preparation depends on the size of the post to be placed.

In view of the foregoing, there is an ongoing need for kits and methods which would simplify the process of placing a dental post.

BRIEF SUMMARY OF THE PREFERRED EMBODIMENTS

The present invention is directed to a kit of dental sub-kits for use in placing a dental post in a prepared recess (e.g., a root canal) of a person's tooth. The kit includes a tray having an interior recess configured to removably receive therein a plurality of individual dental sub-kits. Each sub-kit may have an associated color, number, letter, or other marking to distinguish it from at least one other sub-kit within the kit. The color or marking associated with each sub-kit identifies the size of components contained within the sub-kit. Each sub-kit includes a finishing drill and one or more permanent dental posts. Each sub-kit may optionally include one or more starter drills and/or a dental post analog.

Each sub-kit may include a container having an interior, means for suspending (e.g., a foam material, molded plastic with through-holes, or other suspending, holding and/or organizing structure) the sub-kit contents within the container, and a tethered or removable lid.

One example of the finishing drill may include a metallic shaft having a proximal portion and a distal cutting portion, a smooth heat generating tip at the end of the distal portion, and a central abrasive portion between the proximal end and the distal end. In use the finishing drill is configured to form a bore at least approximately corresponding to the size, shape, and length of a selected permanent dental post.

Each permanent dental post included within each sub-kit includes a distal insertion portion for insertion into a prepared recess of a tooth and a proximal portion extending beyond the distal insertion portion. Permanent dental posts may be formed of any suitable material. According to one embodiment the permanent dental posts comprise a metal or fiber material (e.g., carbon or quartz fiber composite).

In some cases, the sub-kits within the kit may be disposable. Alternatively the sub-kits may be autoclavable so as to allow for cleaning and reuse.

The kit of dental sub-kits may be used for placing a dental post within a prepared recess of a tooth. According to one embodiment, a dental practitioner selects a dental sub-kit from the plurality of sub-kits containing components of a desired size, the dental practitioner then uses a finishing drill from the selected dental sub-kit to prepare the recess of a tooth for insertion of a dental post. The dental practitioner then inserts a permanent dental post from the selected dental sub-kit into the prepared recess of a tooth.

If provided, a starter drill and/or a dental post analog may be used in preparation for placement of a permanent dental post. The dental practitioner may use a starter drill from the selected sub-kit to remove the coronal gutta-percha within the packed and sealed tooth recess to make an initial enlargement of the canal, while a dental post analog may be used as a try-in to verify or determine the correct size, girth, and length of permanent dental post to be used. Once a permanent dental post has been inserted into the prepared tooth recess, a core and dental prosthesis may be formed and fitted over the inserted permanent dental post.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The present invention is directed to a kit of dental sub-kits for use in placing a dental post in a person's tooth. The kit includes a tray having an interior recess configured to removably receive therein a plurality of individual dental sub-kits. Each sub-kit may have an associated color, number, letter, or other marking to distinguish it from at least one other sub-kit within the kit. The color or marking associated with each sub-kit identifies the size of components contained within the sub-kit. Each sub-kit includes a finishing drill and one or more permanent dental posts. Each sub-kit may optionally include a starter drill and/or a dental post analog.

II. Exemplary Kits of Sub-Kits for Dental Surgery

Figure 1:
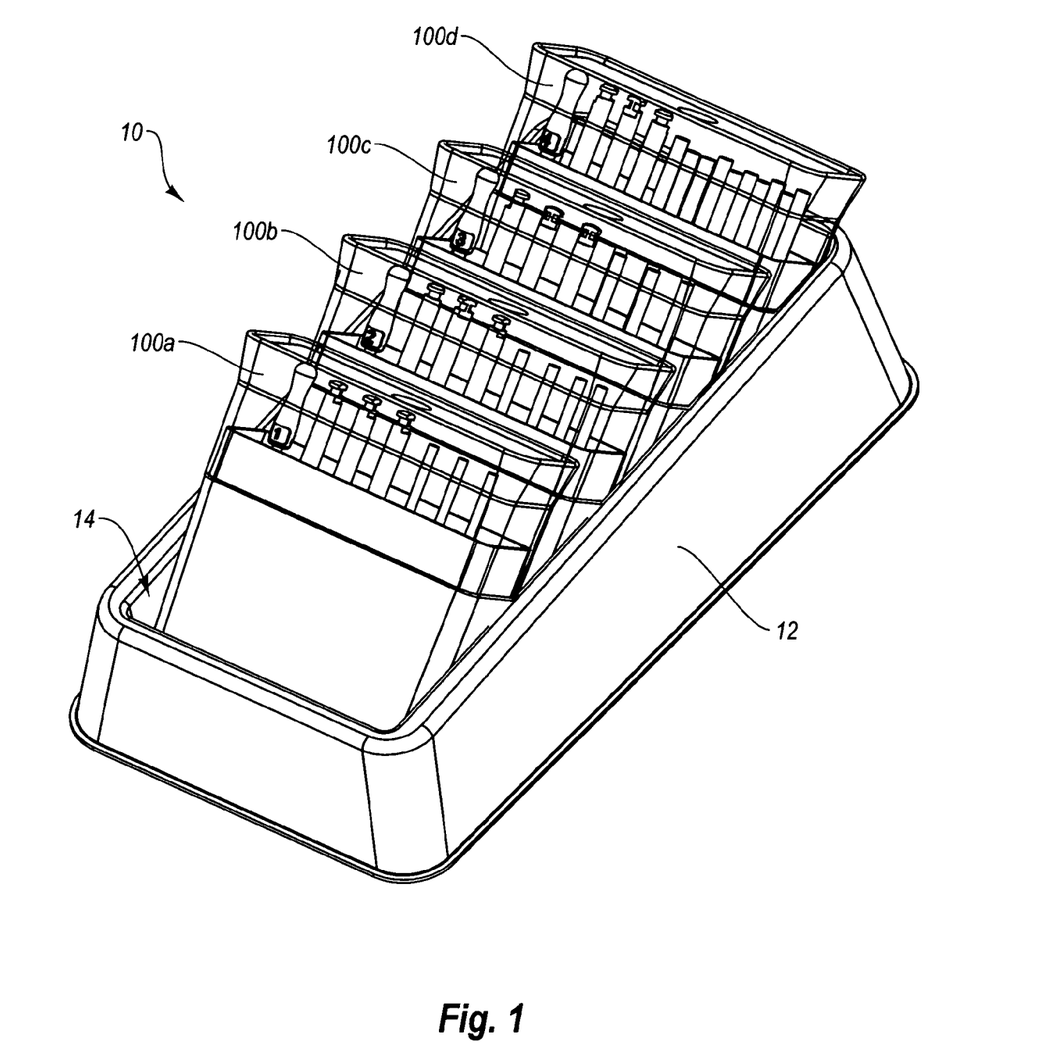
FIG. 1 is a perspective view of an exemplary kit of sub-kits for dental surgery.

FIG. 1 illustrates an exemplary kit 10 of sub-kits (e.g., 100a, 100b, 100c, and 100d) for placing a dental post in a prepared recess of a person's tooth. Kit 10 includes a tray 12 having an interior recess 14 configured to removeably receive a plurality of individual sub-kits (e.g., 100a, 100b, 100c, and 100d). Each sub-kit is of an associated color so as to distinguish it from at least one other sub-kit within the kit. The color associated with each sub-kit identifies the size of components contained within the sub-kit. For example, a yellow sub-kit may contain components for use with relatively small root canals, red and blue sub-kits may contain components for use with intermediate size root canals, while a green sub-kit may contain components for use with relatively large root canals.

Figure 2:
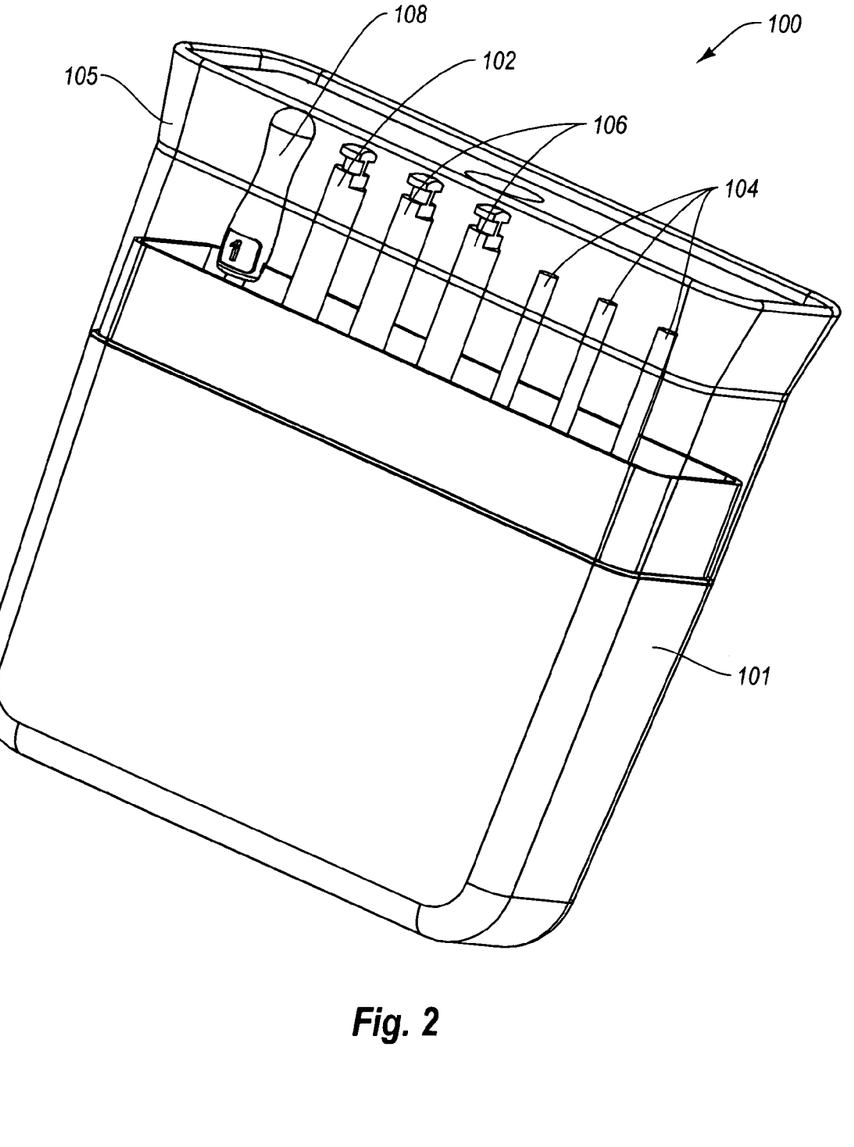
FIG. 2 is a close up perspective view of one of the sub-kits of FIG. 1.

Each sub-kit includes a finishing drill 102 and a plurality of permanent dental posts 104. An exemplary sub-kit 100 is perhaps best seen in FIG. 2. Sub-kit 100 illustrated in FIG. 2 includes a container 101 having an interior, a foam material (not shown) for suspending and maintaining the contents of sub-kit 100 within container 101, and a removable lid 105. Illustrated sub-kit 100 includes one finishing drill 102, three permanent dental posts 104, two optional starter drills 106, and an optional dental post analog 108. Although illustrated with specific numbers of the various components (e.g., one finishing drill, three permanent dental posts, two starter drills, and one dental post analog), any number of each may be provided, as desired.

A. An Exemplary Finishing Drill

Figure 3A:
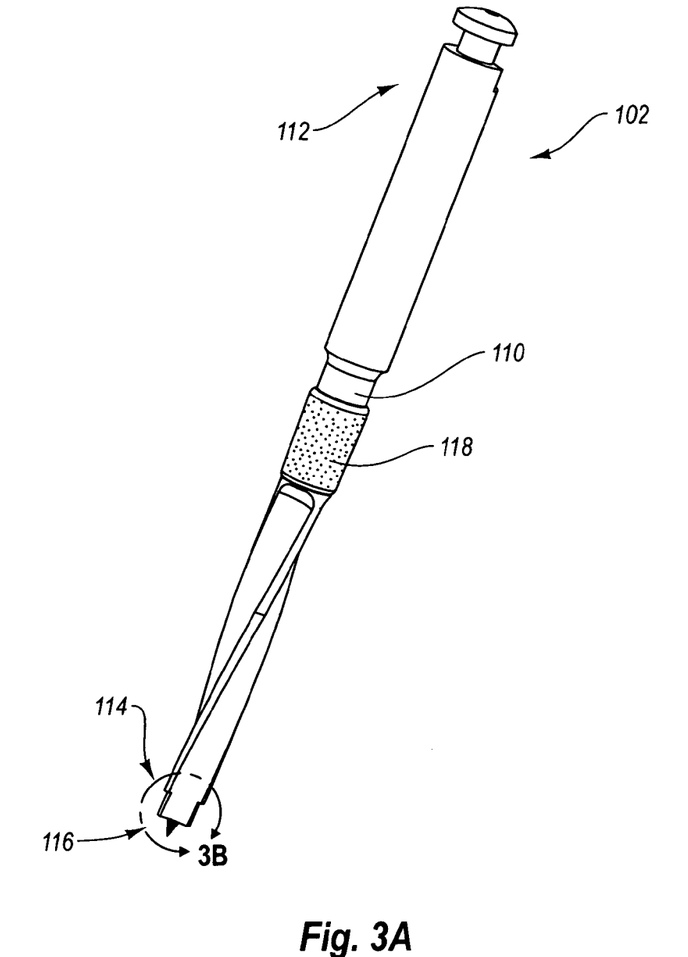
FIG. 3A is a perspective view of an exemplary finishing drill.
Figure 3B:
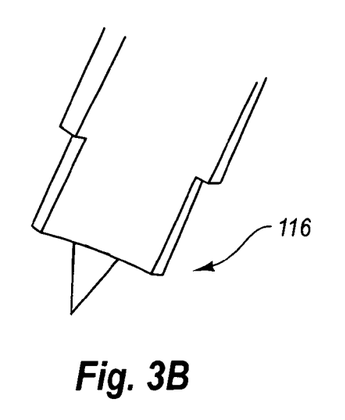
FIG. 3B is a close up perspective view of the distal tip of the finishing drill of FIG. 3A.

FIGS. 3A and 3B illustrate an exemplary finishing drill 102. Finishing drill 102 includes a metallic shaft 110 having a proximal portion 112 configured for attachment to a dental head piece, and a distal cutting portion 114. Finishing drill 102 also includes a smooth heat generating tip 116 (shown in close up in FIG. 3B) at the end of distal portion 114 and a central abrasive portion 118 located between proximal portion 112 and distal cutting portion 114. In use, finishing drill 102 is configured to form a bore that at least approximately corresponds to the size, shape, and length of the permanent dental post(s) also included within same sub-kit 100.

FIG. 3B illustrates a close up perspective view of heat generating tip 116. Additional details regarding heat generating tip 116, and exemplary embodiments of finishing drills are disclosed in U.S. Patent Application Publication 2004/0081940, herein incorporated by reference with respect to its disclosure of finishing drills. Exemplary finishing drills are sold under the trade name GYROTIP by MTI Precision Products LLC, located in Lakewood, N.J.

B. An Exemplary Permanent Dental Post

Figure 4:
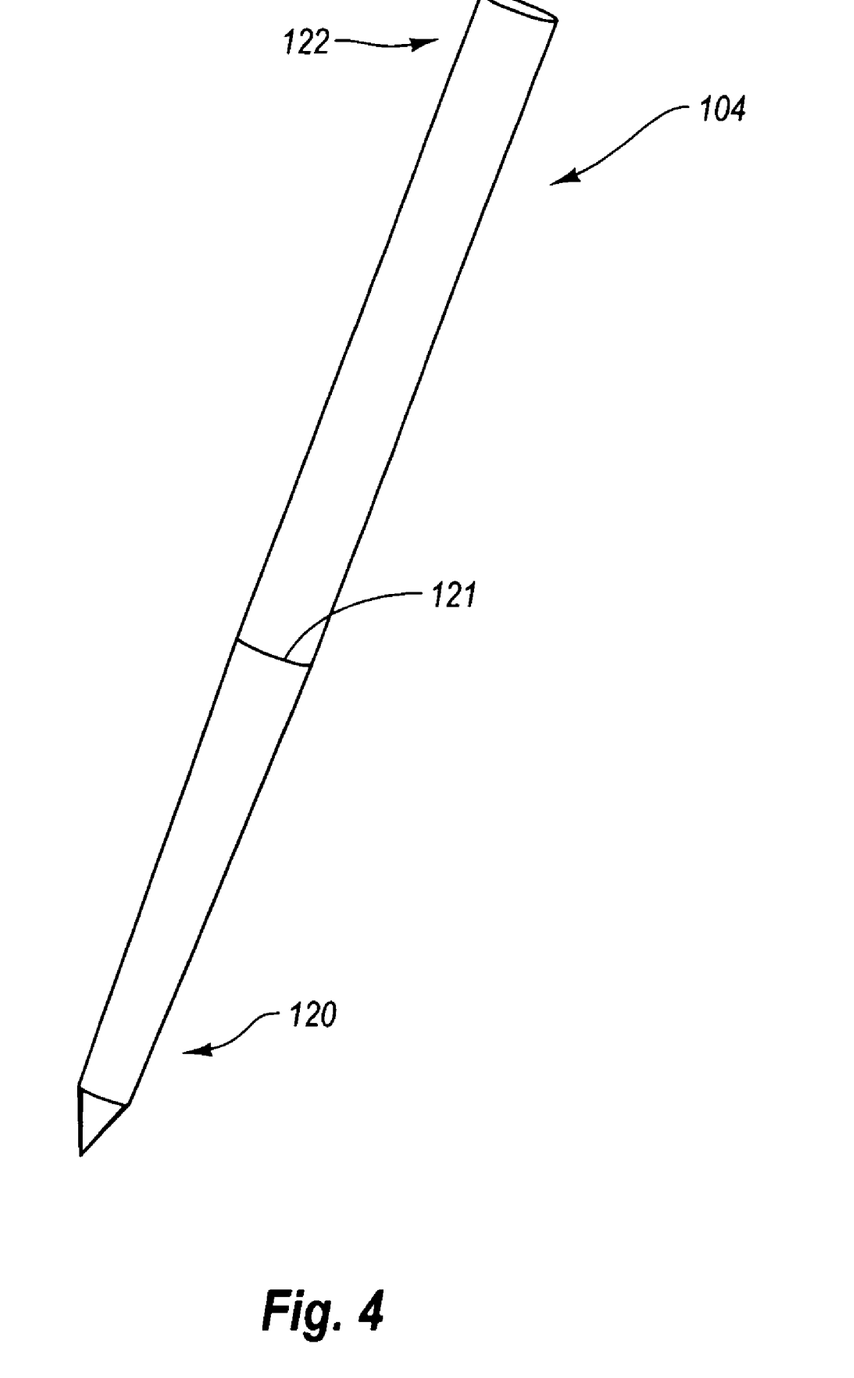
FIG. 4 is a perspective view of an exemplary permanent dental post.

FIG. 4 illustrates one embodiment of an exemplary permanent dental post 104. Permanent dental post 104 includes a distal insertion portion 120 for insertion into a prepared recess of a tooth (e.g., a root canal). Permanent dental post 104 also includes a proximal portion 122 which extends beyond distal insertion portion 120. The distal insertion portion 120 includes a tapered portion (beginning at 121) and a non-tapered parallel portion which extends up through proximal portion 122.

Permanent dental posts included in the sub-kits of the present invention may comprise any suitable material. According to one preferred embodiment, permanent dental post 104 comprises a metal or fiber material (e.g., carbon or quartz fiber composite). Exemplary permanent dental posts are sold by RTD, located in Grenoble, France.

C. An Exemplary Starter Drill

Figure 5:
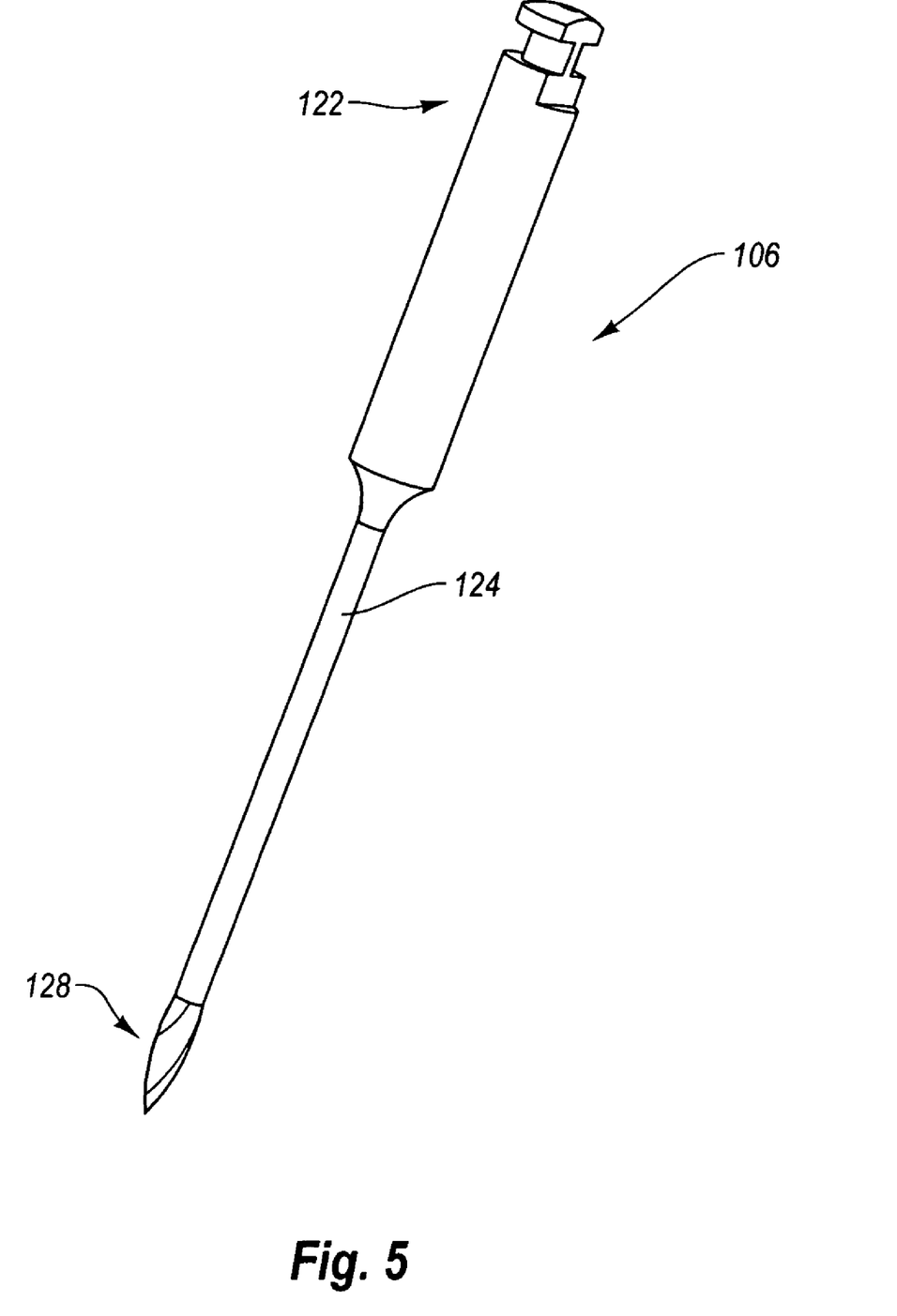
FIG. 5 is a perspective view of an exemplary starter drill.

FIG. 5 illustrates an exemplary starter drill 106. Exemplary starter drill 106 includes a metallic shaft 124 having a proximal portion 126 configured for attachment to a dental head piece, and a distal cutting portion 128, which may be bulbous, as illustrated. Starter drill 106 may be useful for removing coronal gutta-percha prior to use of finishing drill 102. Exemplary starter drills (e.g., Gates Glidden) are sold by Brasseler USA, located in Savannah, Ga.

D. An Exemplary Dental Post Analog

Figure 6:
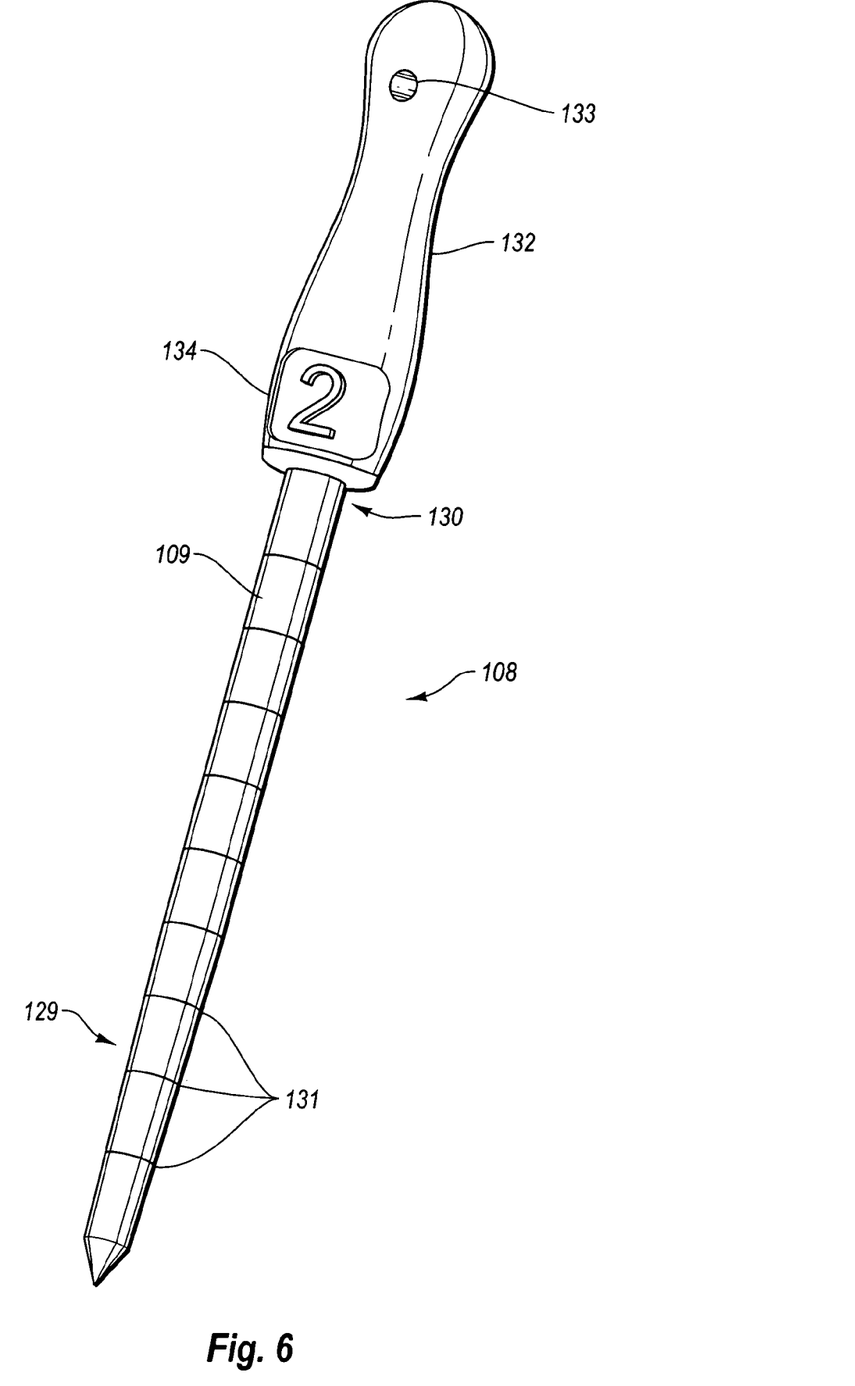
FIG. 6 is a perspective view of an exemplary dental post analog.

FIG. 6 illustrates an exemplary dental post analog 108. Dental post analog 108 includes an analog post body 109. Post body 109 includes a distal insertion portion 129 and a proximal portion 130 extending beyond distal insertion portion 129. The distal insertion portion 129 at least approximately corresponds in size, shape, and length to a permanent dental post (e.g., permanent dental post 104). Distal insertion portion 129 is configured for temporary insertion into a prepared recess of a tooth.

Analog post body 109 also includes at least one of means for determining the depth of placement of the distal insertion portion, means for gripping the post body, or means for tethering the post body. The illustrated embodiment of dental post analog 108 includes markings 131 formed along distal insertion portion 129. Markings 131 are one example of means for determining the depth of placement of the distal insertion portion. Alternative examples of means for determining the depth of placement of the distal insertion portion include one or more circumferential grooves formed within the distal insertion portion or one or more circumferential ridges formed within the distal insertion portion.

Dental post analog 108 may include means for gripping analog post body 109. The embodiment illustrated in FIG. 6 includes a handle 132 formed near a proximal end of proximal portion 130 of post body 109. Handle 132 is one example of means for gripping analog post body 109.

Dental post analog 108 may also include means for tethering post body 109. The embodiment illustrated in FIG. 6 includes a hole 133 formed through the proximal portion of handle 132. A string or other flexible leash can be inserted into hole 133 for tethering post body 109 as a safety measure (e.g., to prevent inadvertent swallowing of or chocking on post body 109). Hole 133 is one example of means for tethering post body 109.

Dental post analog 108 may include coding means for identifying the size of dental post analog 108. Number 134 is one example of means for coding. A letter or other marking may alternatively be used. In some cases, coding means for identifying the size of dental post analog 108 may comprise forming at least a portion of post body 109 so as to be of a selected color, preferably the same color associated with the selected sub-kit (e.g., yellow may signify the smallest size, red and blue may signify or identify intermediate sizes, while green may signify a largest size).

The dental post analogs may be formed from any suitable material. Exemplary materials include, but are not limited to, thermoplastic materials, thermoset materials, ceramics, or metals.

According to one embodiment, at least the distal insertion portion 129 of post body 109 may be formed of a material that is radiopaque. Such an embodiment allows a dental practitioner to see the location of a dental post analog while inserted into a prepared recess of a tooth by x-ray or other radiograph.

The contents of each sub-kit, including the finishing drill, any optional starter drills and/or dental post analogs, and even the permanent dental posts may be autoclavable, so as to allow for cleaning and reuse of the sub-kit components. Alternatively, the sub-kit and its contents may be disposable.

III. Exemplary Methods of Use

Figure 7:
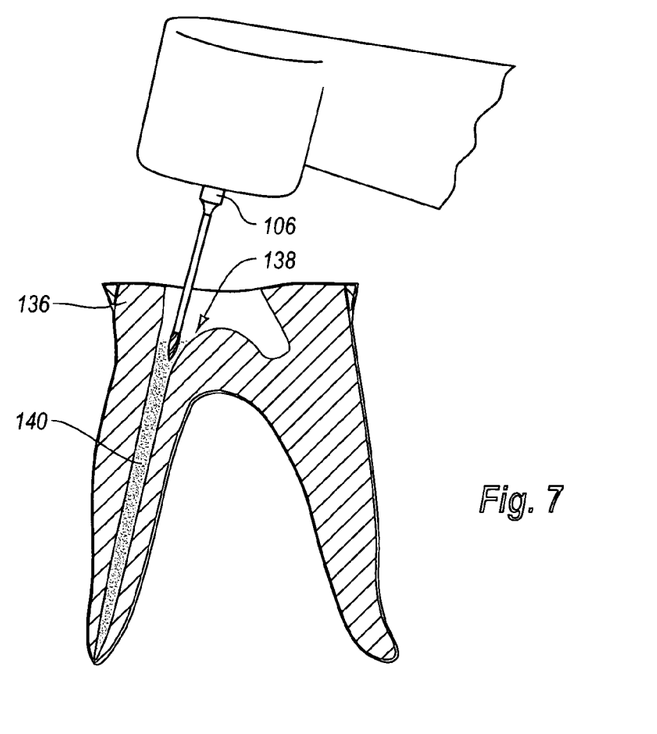
FIG. 7 illustrates use of the starter drill of FIG. 5 to remove coronal gutta-percha from a packed and sealed recess of a tooth prior to insertion of a dental post.

FIG. 7 illustrates a tooth 136 which has been broken down in preparation for fitting of a dental prosthesis (e.g., a crown). Prepared tooth recess 138 (e.g., a root canal) has been reamed out to remove nerve and other tissue, while also increasing the size of recess 138 in preparation to installing a dental post and dental prosthesis. The tooth recess 138 has also been packed and sealed with packing material 140 (e.g., gutta-percha).

Figure 8:
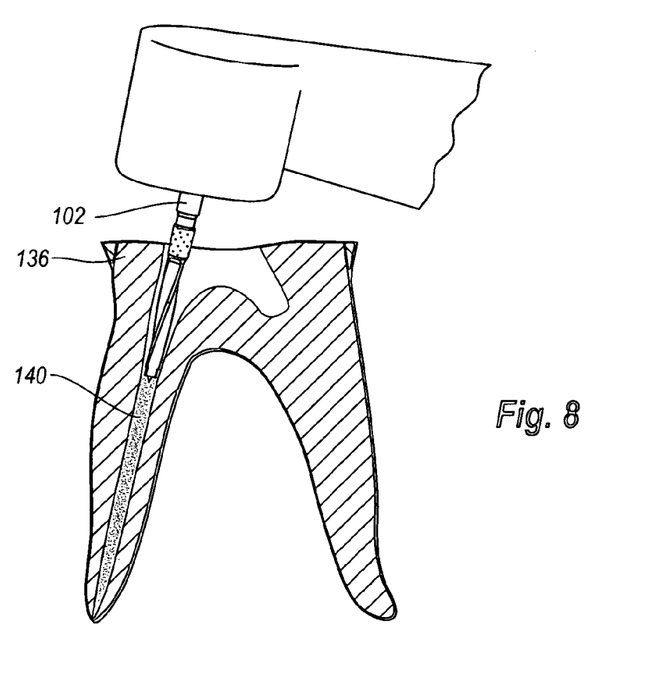
FIG. 8 illustrates use of the finishing drill of FIG. 3A to remove gutta percha as to prepare a recess of a tooth for insertion of a dental post.

In order to prepare tooth recess 138 for insertion of a permanent dental post, starter drill 106 may be used to remove the coronal gutta-percha or other packing material 140 down to the root canal orifice. Once the coronal gutta-percha has been removed, a finishing drill 102 may be used to remove additional packing material, while slightly widening the width of recess 138 down to a desired depth as illustrated in FIG. 8. The removal of packing material 140, and slight widening and shaping of tooth recess 138 prepares recess 138 to receive a permanent dental post. Use of starter drill 106 is optional, i.e., finishing drill 102 may be used to remove any needed packing material 140, without the use of starter drill 106.

Figure 9A:
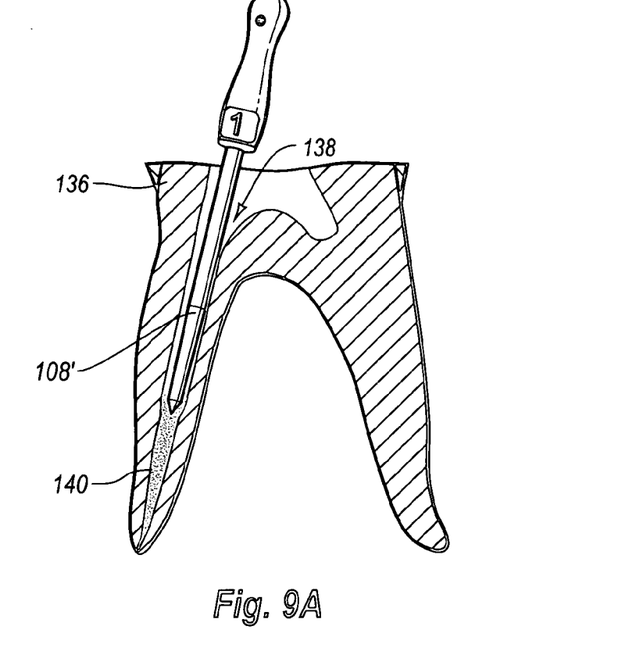
FIGS. 9A-9B illustrate a method of using a dental post analog as a try-in for a permanent dental post.
Figure 9B:
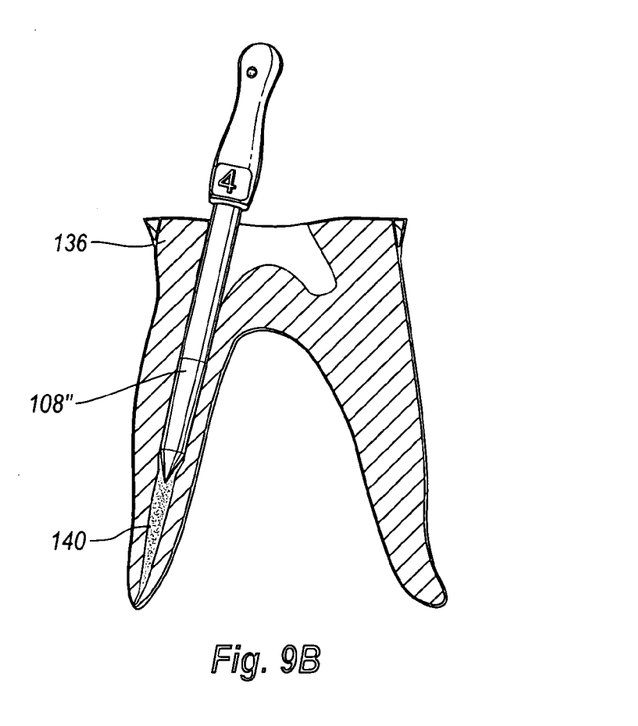

As illustrated in FIGS. 9A and 9B the dental post analog or analogs may be used as a try-in for determining the size, girth, and length of a correctly sized permanent dental post. In this procedure, a dental practitioner selects a dental post analog of a desired size, and as illustrated in FIG. 9A, the dental post analog 108' is inserted into prepared tooth recess 138 of tooth 136 on a trial basis to determine whether inserted dental post analog 108' corresponds to a correctly sized permanent dental post. FIG. 9A illustrates insertion of a dental post analog 108' which is too narrow. The dental practitioner may continue to insert incrementally larger sized dental post analogs until the correctly sized post analog is identified. FIG. 9B illustrates insertion of a thicker dental post analog 108", which is correctly sized with respect to tooth recess 138. Using one or more dental post analogs as try-ins aids the dental practitioner in determining which size of permanent dental post should be used. Use of the dental post analogs allows the dental practitioner to do so inexpensively and conveniently with a disposable or autoclavable dental post analog. In addition, the procedure can be performed without contaminating the permanent dental posts during a try-in procedure. Once removed, the dental post analog may either be discarded or autoclaved, as desired.

Figure 10:
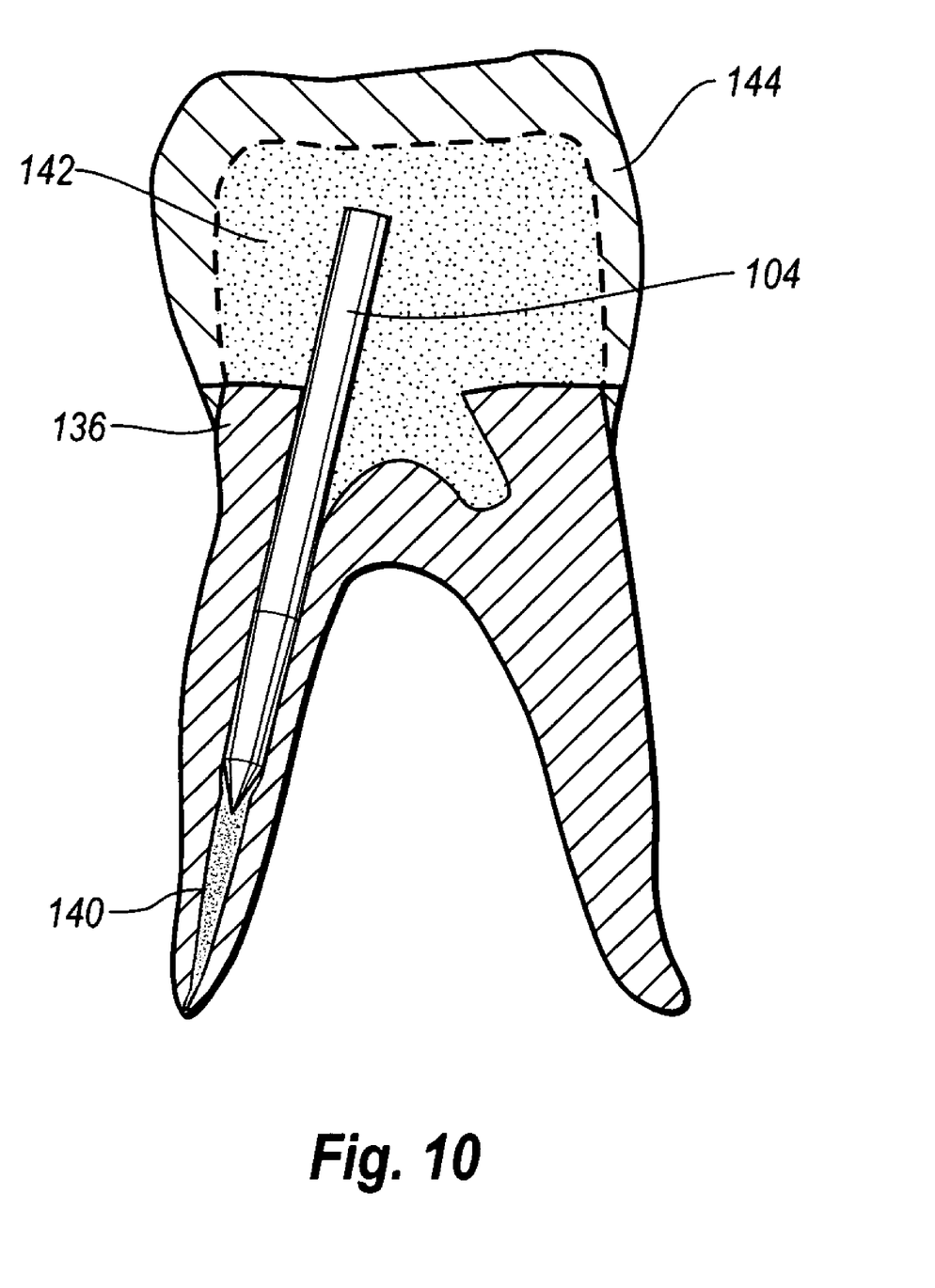
FIG. 10 illustrates a completed dental restoration including a permanent dental post, a core, and a crown.

A dental prosthesis 144 (e.g., a crown) and supporting core 142 may then be formed, fitted, and bonded, cemented, or otherwise placed over inserted and bonded permanent dental post 104. Methods for forming and placing a supporting core 142 and a dental prosthesis 144 will be known to those skilled in the art. Additional methods for forming and placing a core and dental prosthesis employing the dental post analogs optionally included in each sub-kit are disclosed in U.S. application Ser. No. 11/094,991 filed Mar. 31, 2005, hereby incorporated by reference in its entirety.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A kit of dental sub-kits for use in placing a dental post in a person's tooth comprising:
   a tray having an interior recess configured to removably receive therein a plurality of sub-kit containers, each containing therein a dental sub-kit comprised of sub-kit components of related size, each sub-kit container having an associated color, number, letter, or other marking relating to size of the sub-kit components contained therein that distinguishes it from at least one other sub-kit container having sub-kit components of a different size the kit, each sub-kit comprising:
   a finishing drill comprised of:
      a metallic shaft, said shaft having a proximal portion and a distal cutting portion;
      in use said finishing drill forming a bore at least approximately corresponding to the size, shape, and length of a selected permanent dental post; and
   at least one permanent dental post comprising a distal insertion portion for insertion into a prepared recess of a tooth and a proximal portion extending beyond said distal insertion portion;
   each of said finishing drill and said at least one permanent dental post including an associated color, number, letter, or other marking relating to size that differs from an associated color, number, letter, or other marking relating to a different size of a finishing drill and permanent dental post of at least one other sub-kit of the kit.

2. A kit of dental sub-kits as recited in claim 1, each sub-kit container further comprising an interior, means for suspending sub-kit components within said container, and a tethered or removable lid.

3. A kit of dental sub-kits as recited in claim 1, wherein each of said permanent dental posts comprises a metal or fiber material.

4. A kit of dental sub-kits as recited in claim 1, wherein each of said permanent dental posts comprises carbon or quartz fiber composite material.

5. A kit of dental sub-kits as recited in claim 1, at least one of said sub-kits further comprising at least one starter drill which has a shaft and an enlarged cutting portion and includes the associated color, number, letter, or other marking relating to the size of the finishing drill and dental post of the sub-kit.

6. A kit of dental sub-kits as recited in claim 5, at least one of said sub-kits further comprising at least one dental post analog which has means for determining depth of placement in a root canal and includes said associated color, number, letter, or other marking relating to the size of said finishing drill, dental post and starter drill of said sub-kit, said dental post analog comprising a post body comprising:
   a distal insertion portion, at least approximately corresponding to the size, shape, and length of a permanent dental post, for temporary insertion into a prepared recess of a tooth; and
   a proximal portion extending beyond said distal insertion portion.

7. A kit of dental sub-kits as recited in claim 6, wherein each of said dental post analogs comprises at least one of a thermoplastic material, a thermoset material, a ceramic, or a metal.

8. A kit of dental sub-kits as recited in claim 6, wherein at least said distal insertion portion of said post body is radiopaque.

9. A kit of dental sub-kits as recited in claim 6, wherein said analog post body comprises means for determining the depth of placement of said distal insertion portion, said means for determining the depth of placement of the distal insertion portion comprising one or more of circumferential grooves, ridges, or markings formed within said distal insertion portion.

10. A kit of dental sub-kits as recited in claim 6, wherein said dental post analog comprises means for gripping said post body, said means for gripping said post body comprising a handle formed near a proximal end of said proximal portion of said post body.

11. A kit of dental sub-kits as recited in claim 6, wherein said dental post analog comprises means for tethering said post body, said means for tethering said post body comprising a hole formed through the proximal portion of said post body.

12. A kit of dental sub-kits as recited in claim 1, wherein said sub-kits are disposable.

13. A kit of dental sub-kits as recited in claim 1, wherein said sub-kits are autoclavable.

14. A kit of dental sub-kits for use in placing a dental post in a person's tooth comprising:
a tray having an interior recess configured to removably receive therein a plurality of individual dental sub-kits, each sub-kit having an associated color, number, letter, or other marking relating to size that distinguishes it from at least one other sub-kit within the kit, each sub-kit comprising:
a finishing drill comprised of:
a metallic shaft, said shaft having a proximal portion and a distal cutting portion;
a smooth, heat generating tip at the end of said distal portion;
a central abrasive portion between said proximal end and said distal end; and
in use said finishing drill forming a bore at least approximately corresponding to the size, shape, and length of a selected permanent dental post;
at least one permanent dental post comprising a distal insertion portion for insertion into a prepared recess of a tooth and a proximal portion extending beyond said distal insertion portion; and
at least one of:
a starter drill having a shaft and an enlarged cutting portion or
a dental post analog having means for determining depth of placement of the post analog in a root canal, a distal insertion portion, at least approximately corresponding to the size, shape, and length of a permanent dental post, and a proximal portion extending beyond said distal insertion portion,
each of said finishing drill, said at least one permanent dental post, and said at least one of a starter drill or dental post analog including an associated color, number, letter, or other marking relating to size that differs from an associated color, number, letter, or other marking relating to a different size of a finishing drill and permanent dental post of at least one other sub-kit of the kit.

15. A method of using, sterilizing and reassembling a kit of dental sub-kits for placement of a dental post, comprising:
providing a kit of dental sub-kits for placement of a dental post comprising:
a tray having an interior recess configured to removably receive therein a plurality of individual dental sub-kits, each sub-kit having an associated color, number, letter, or other marking relating to size that distinguishes it from at least one other sub-kit within said kit, each sub-kit comprising:
a finishing drill; and
one or more permanent dental posts, each comprising a distal insertion portion for insertion into a prepared recess of a tooth and a proximal portion extending beyond said distal insertion portion;
each of said finishing drill and said at least one permanent dental post including an associated color, number, letter, or other marking relating to size that differs from an associated color, number, letter, or other marking relating to a different size of a finishing drill and permanent dental post of at least one other sub-kit of the kit;
removing and using a plurality of differently-sized finishing drills from a plurality of dental sub-kits to prepare tooth recesses for insertion of a dental posts therein;
removing and using a plurality of differently-sized permanent dental posts from the plurality of dental sub-kits;
sterilizing at least some of the differently-sized finishing drills and permanent dental posts removed from the dental sub-kits that remain; and
reassembling at least a portion of the kit of dental sub-kits by matching similarly sized sterilized drills and permanent dental posts by the associated color, number, letter or other marking.

16. A method as recited in claim 15, wherein said prepared recess of a tooth is a post canal.

17. A method as recited in claim 15, wherein said selected dental sub-kit further comprises a starter drill having a shaft, an enlarged cutting portion and said associated color, number, letter, or other marking relating to size, said method further comprising using said starter drill from said selected dental sub-kit to remove coronal packing material from said recess of a tooth prior to using said finishing drill to complete preparation of said tooth recess.

18. A method as recited in claim 15, wherein said selected dental sub-kit further comprises a dental post analog having means for determining depth of placement in a root canal and said associated color, number, letter, or other marking relating to size, said method further comprising inserting said dental post analog from said selected dental sub-kit into a prepared tooth recess on a trial basis to determine whether said inserted dental post analog corresponds in size to a correctly sized permanent dental post.

19. A method as recited in claim 15, further comprising forming a core and placing a dental prosthesis over said inserted permanent dental post.

20. A method as recited in claim 15, said sterilizing comprising autoclaving.

* * * * *

UNITED STATES PATENT AND TRADEMARK OFFICE
CERTIFICATE OF CORRECTION

PATENT NO. : 7,278,852 B2  Page 1 of 1
APPLICATION NO. : 11/097631
DATED : October 9, 2007
INVENTOR(S) : Dan E. Fischer It is certified that error appears in the above-identified patent and that said Letters Patent is hereby corrected as shown below:

<u>Drawings</u>
Sheet 5, change reference "122" to --126--

<u>Column 6</u>
Line 19, remove "the kit"

<u>Column 8</u>
Line 27, remove "a"

Signed and Sealed this

Twenty-sixth Day of August, 2008

JON W. DUDAS
*Director of the United States Patent and Trademark Office*